United States Patent [19]
Jousson

[11] Patent Number: 5,368,548
[45] Date of Patent: * Nov. 29, 1994

[54] HYDRAULIC APPARATUS FOR BODILY CARE, IN PARTICULAR ORAL CARE

[75] Inventor: Jean-Pierre Jousson, Geneva, Switzerland

[73] Assignee: Les Produits Associes LPA-Broxo S.A., Geneva, Switzerland

[ * ] Notice: The portion of the term of this patent subsequent to Nov. 2, 2010 has been disclaimed.

[21] Appl. No.: 93,327

[22] Filed: Jul. 19, 1993

Related U.S. Application Data

[62] Division of Ser. No. 963,609, Oct. 20, 1992, Pat. No. 5,257,933.

[30] Foreign Application Priority Data

Nov. 7, 1991 [EP] European Pat. Off. ......... 91810861.4

[51] Int. Cl.⁵ .............................................. A61H 9/00
[52] U.S. Cl. ................................................. 601/162
[58] Field of Search ................ 433/80, 81, 82, 84, 433/85; 128/66; 601/162, 163, 164, 165

[56] References Cited

U.S. PATENT DOCUMENTS

| | | | |
|---|---|---|---|
| Re. 27,274 | 1/1972 | Mattingly | 128/66 |
| 3,420,228 | 1/1969 | Kalbfeld | 128/66 |
| 3,495,587 | 2/1970 | Freedman | 128/66 |
| 3,545,645 | 12/1970 | Smith | 220/671 |
| 3,578,884 | 5/1971 | Jacobson | 128/66 |
| 4,770,632 | 9/1988 | Ryder et al. | 433/80 |
| 4,830,032 | 5/1989 | Jousson | 132/323 |
| 4,880,382 | 11/1989 | Moret et al. | 229/449 |
| 4,907,744 | 3/1990 | Jousson | 239/449 |
| 4,989,590 | 2/1991 | Baum et al. | 128/66 |
| 5,029,576 | 7/1991 | Evans, Sr. | 433/80 |
| 5,062,795 | 11/1991 | Woog | 433/80 |

FOREIGN PATENT DOCUMENTS

| | | |
|---|---|---|
| 0267095 | 5/1988 | European Pat. Off. . |
| 0298910 | 1/1989 | European Pat. Off. . |
| 2334336 | 7/1977 | France . |
| 2444441 | 3/1976 | Germany . |

Primary Examiner—John J. Wilson
Attorney, Agent, or Firm—Kane, Dalsimer, Sullivan, Kurucz, Levy, Eisele & Richard

[57] ABSTRACT

The hydraulic apparatus comprises a handpiece connected via a pipe to a pump through an outlet orifice of the casing and a liquid reservoir feeding the pump, in the position of non-utilization the handpiece and the pipe rolled up in a spiral are accommodated on a platform. The end of the pipe connected to the outlet orifice of the casing is installed rotationally movably about the axis of the pipe. Preferably, the platform is itself installed on the casing in a movable manner about an axis perpendicular to the plane of this platform, by a turning adapter mounted in the outlet orifice of the casing.

3 Claims, 9 Drawing Sheets

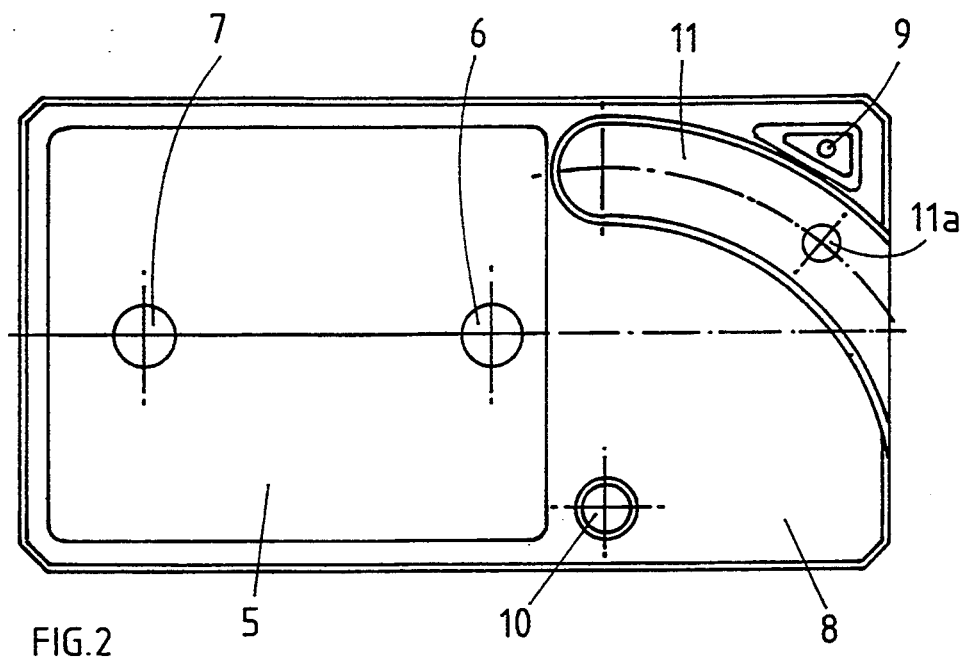
FIG.2
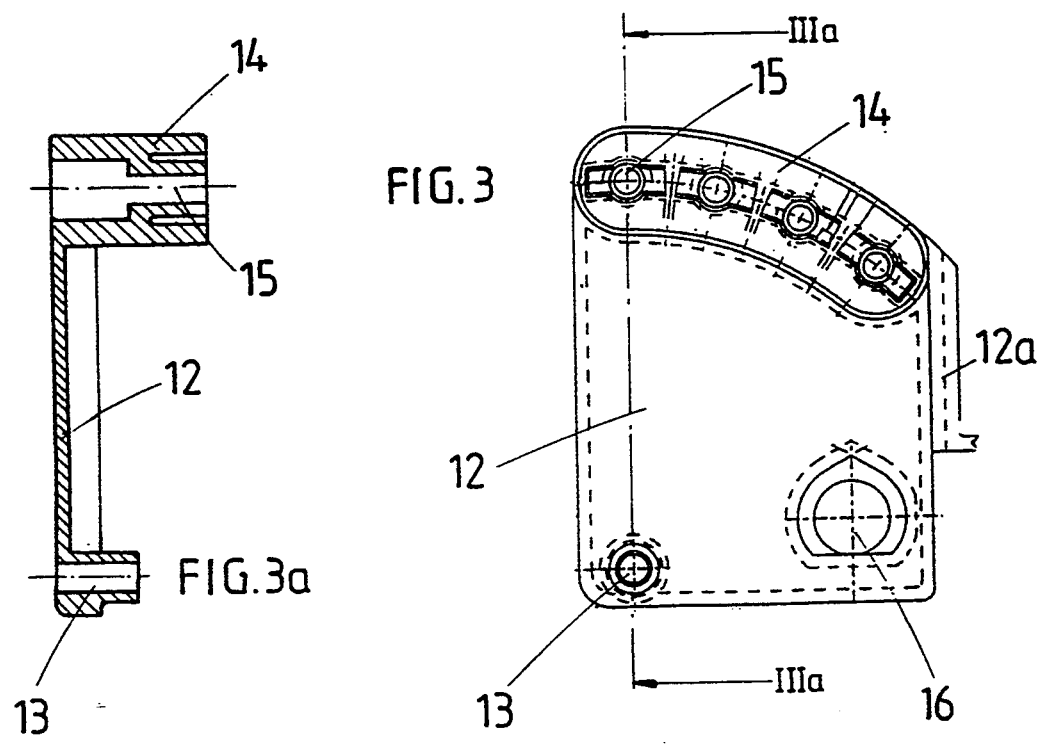
FIG.3
FIG.3a

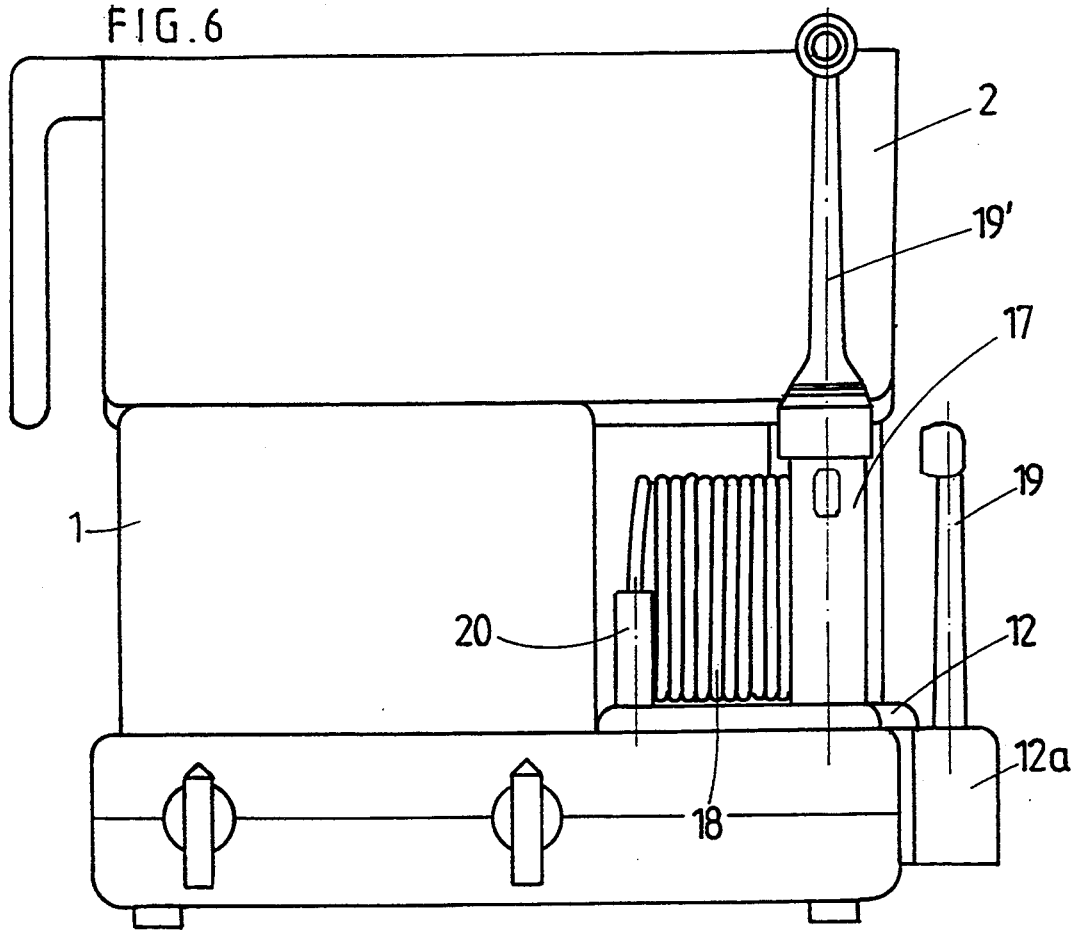
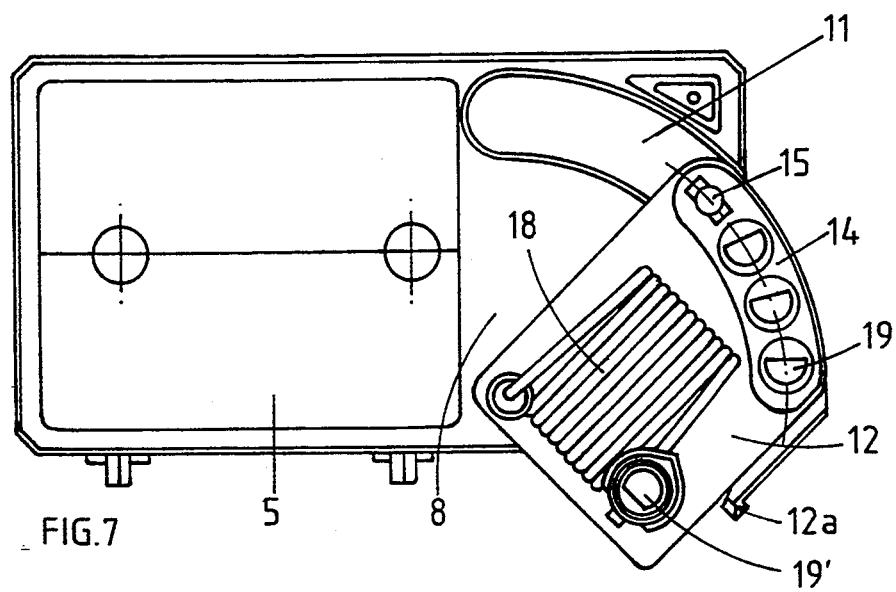

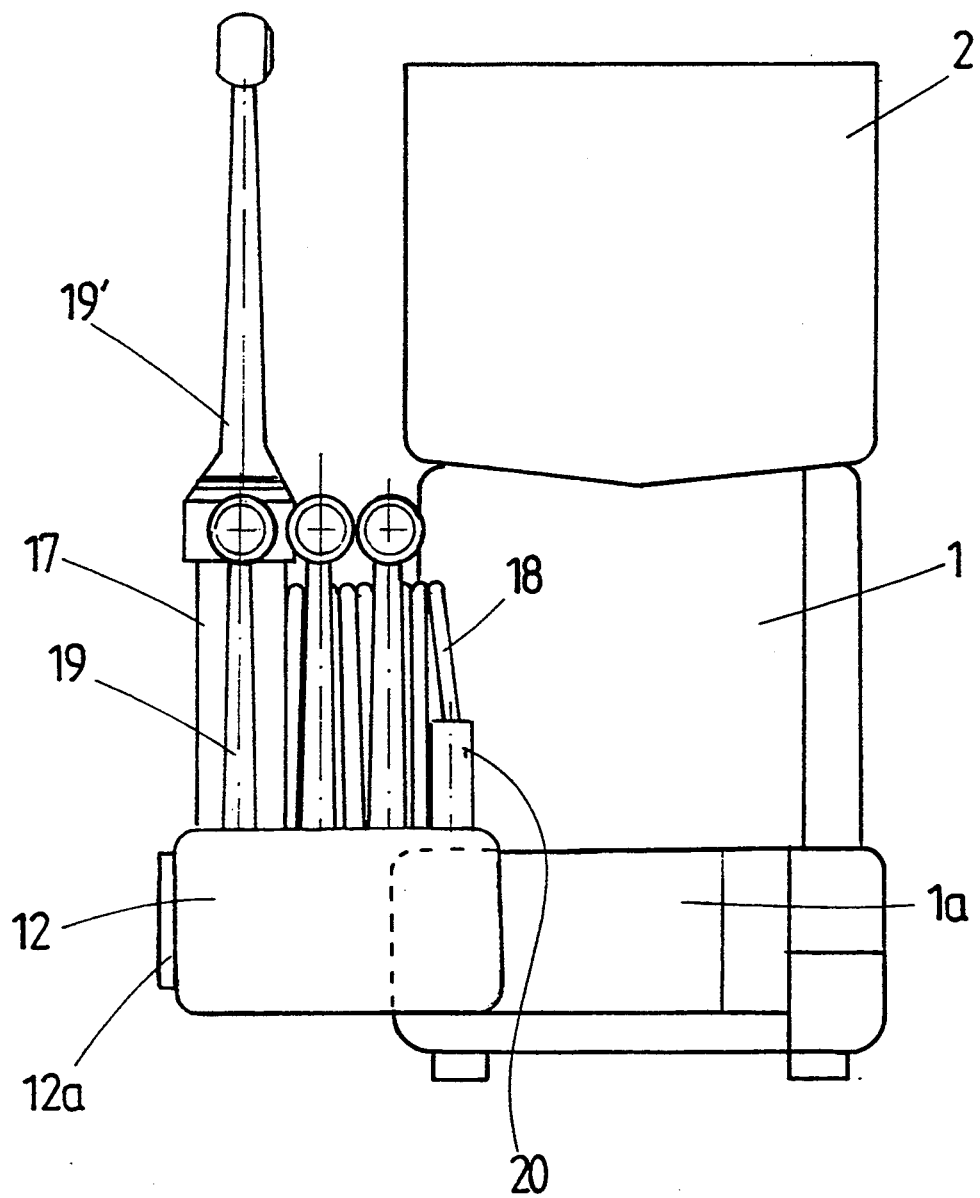

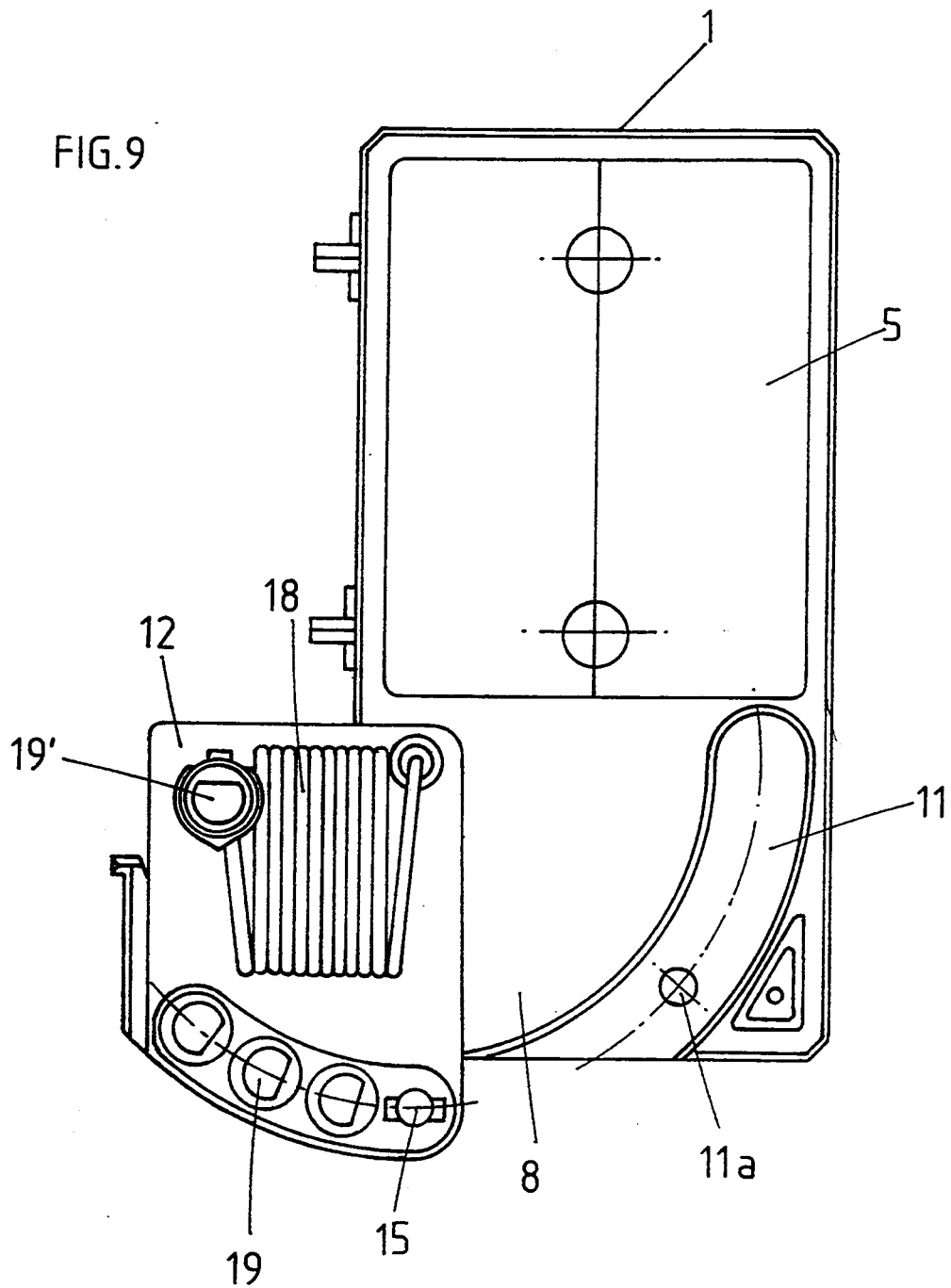

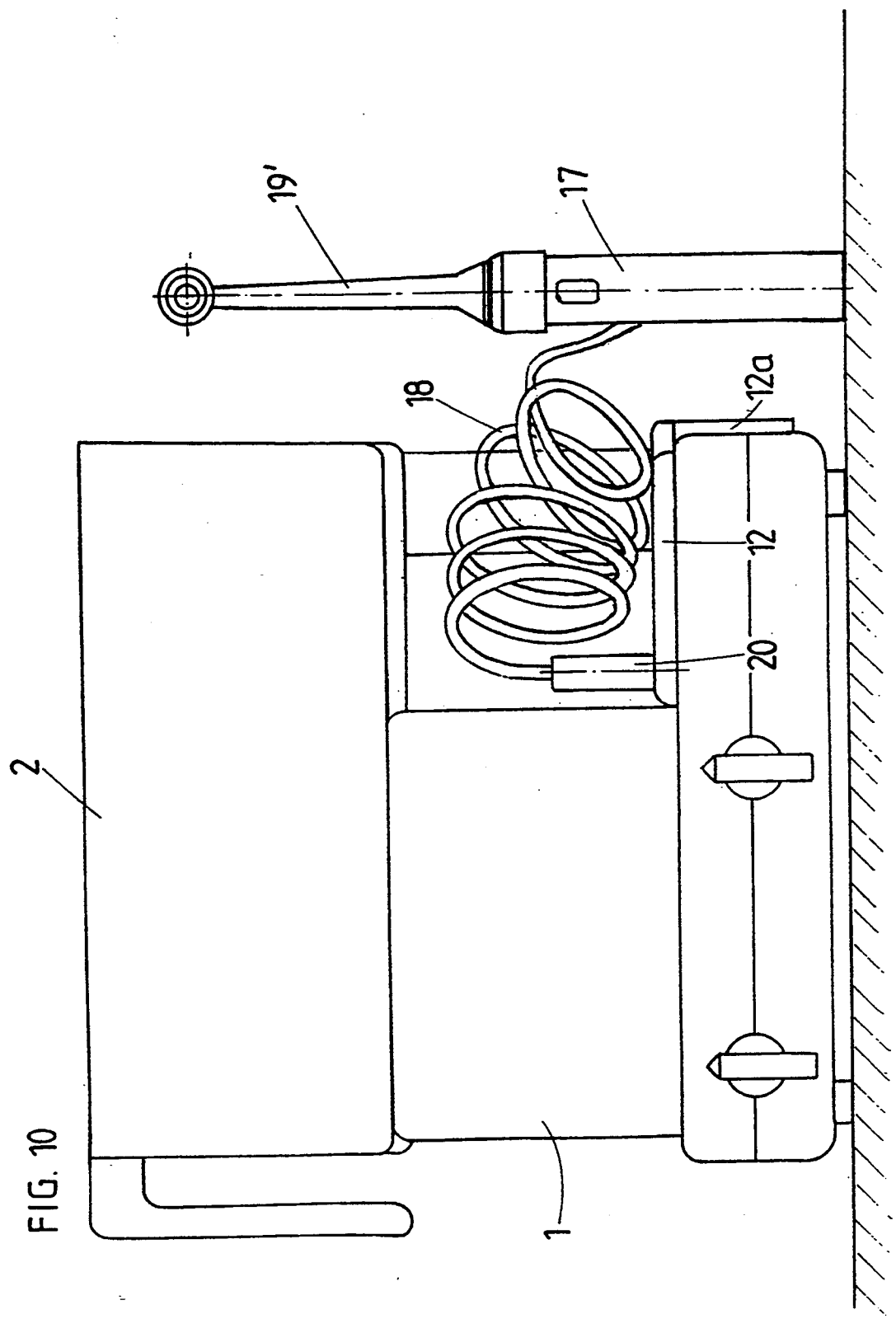

HYDRAULIC APPARATUS FOR BODILY CARE, IN PARTICULAR ORAL CARE

This application is a division of application Ser. No. 07/963,609, filed Oct. 20, 1992, now U.S. Pat. No. 5,257,933.

FIELD OF THE INVENTION

The invention relates to a hydraulic apparatus for bodily care, in particular for oral care, according to the preamble of claim 1 or 2.

PRIOR ART

Such apparatuses equipped with a spraying nozzle are known, for example from U.S. Pat. No. 4,078,558. The platform for housing the pipe in the form of a helical spring (also called very often spiral pipe) and the handpiece which is sunken into an opening of the platform in the rest state of the apparatus is formed by a step offset on the inside of the casing of the apparatus. In general, the arrangement is such that the pipe and the handpiece without nozzle and possibly the nozzles, when placed on this step, do not exceed the external dimensions of the casing. This arrangement is advantageous as far as the storage of the elements of the apparatus during its non-utilization is concerned, and likewise for its transport, because it reduces its bulkiness. By virtue of this arrangement, the reservoir, in the rest state, can be inverted and placed on the casing as a cover.

However, the rigid fixing of the pipe to the outlet orifice of the casing renders the handling of this pipe inconvenient and is a source of noise during functioning of the apparatus. This pipe made of preformed plastic material is quite rigid and, under the action of its prestressing, forms during its non-utilization a helical spring with contiguous turns, the fixed end of the pipe being orientated vertically in general. During utilization, the pipe has to be drawn out to remove it from the casing, but a part remains on the platform and, during the functioning of the apparatus, it can be in contact with one or more places of the casing, which causes an unpleasant noise, the pipe vibrating according to the frequency of the pump and the pulsations of the liquid, in general of approximately 50 Hz, it knocks with this frequency against the casing and, to prevent this noise, the user always has to exert sufficient traction in a well determined direction on the pipe in order to move it away from the casing. Furthermore, this contact of the pipe with the casing can create wear, even a perforation of the pipe.

Moreover, the position of the handpiece and of the pipe accommodated on this step offset on the inside makes their accessibility quite difficult. Since this step is limited on one or more sides by a wall, respectively a number of walls, of the casing, these walls are very close, even in contact with the pipe. If, as is the case in numerous known alternatives, the arrangement of the apparatus is such that, in the working position, the reservoir is arranged above this platform and therefore covers the space in which the pipe, the handpiece and possibly the spare nozzles are situated, the accessibility to these elements and their maintenance are particularly difficult.

With an apparatus of this type, the height of the free space between the platform and the bottom of the reservoir makes it possible to place vertically the handpiece alone, formed by a nozzle-holder, but not the nozzle-holder equipped with a nozzle, the spare nozzles being positioned vertically next to the nozzle-holder on the same platform. For this reason, if the user places the filled reservoir on the casing, the water which leaves the reservoir and passes through the pump can, according to the principle of communicating vessels, rise in the nozzle-holder and flow out at the upper end of the latter, since this end is lower than the height of the water in the reservoir. To avoid this disadvantage, the user must, before placing the filled reservoir, take the nozzle-holder, move it away from the platform and fix the nozzle to it or keep it higher than the reservoir, which is not very convenient.

This known arrangement of the pipe and of the handpiece is therefore capable of hampering the user in his handling operations.

SUMMARY OF THE INVENTION

The aim of the present invention is to facilitate the handling of the handpiece and of its pipe, while retaining reduced bulkiness of the apparatus when it is not used.

This aim is achieved by the characteristics of claim 1 or preferably claim 2.

These arrangements have the following main advantages:

during the functioning of the apparatus, the pipe can be moved away from the casing very easily and no longer touches it, therefore the unpleasant noise and the wear caused by the impacts with the casing are eliminated;

Moreover, with the embodiment according to claim 2:

the handpiece as well as the nozzles or the spare toothbrushes positioned on the platform are much more accessible;

before placing the filled reservoir on the casing, the user need turn the platform simply by a small angle to release the handpiece from the reservoir, which allows him to fix a nozzle to said handpiece without removing it from the platform. This avoids, when the filled reservoir is placed on the casing, a flowing out of the water since the handpiece assembly plus nozzle is higher than the reservoir. The user can also release the platform to a greater extent to make its entire surface accessible. The user can of course make the platform pivot back into its rest position after having taken hold of the handpiece, in order not to be hampered during handling operations.

Preferred embodiments result from the dependent claims.

BRIEF DESCRIPTION OF THE DRAWINGS

The invention will be described in greater detail by means of an example of an apparatus equipped with a nozzle-holder as handpiece and with four nozzles.

FIG. 2 shows a view from above of the casing, with the reservoir and the platform removed.

FIG. 3 is a view from above of the platform alone.

FIG. 3a is a cross-section of the platform along IIIa—IIIa in FIG. 3.

FIG. 6 is a lateral view of the apparatus in a position of preparation, with the platform partially pivoted towards the exterior to make possible the fixing of a nozzle on the handpiece which has remained on the platform.

FIG. 7 is a view from above of the apparatus according to FIG. 6, with the reservoir removed.

FIG. 8 is a lateral view on the narrow side of the apparatus, with the platform completely pivoted towards the outside.

FIG. 9 is a view from above of the apparatus according to FIG. 8, with the reservoir removed.

FIG. 10 is a lateral view of the apparatus in utilization position, with the handpiece moved away from the casing and the platform put back in rest position below the reservoir.

DESCRIPTION OF THE PREFERRED EMBODIMENT(S)

Figure 1:
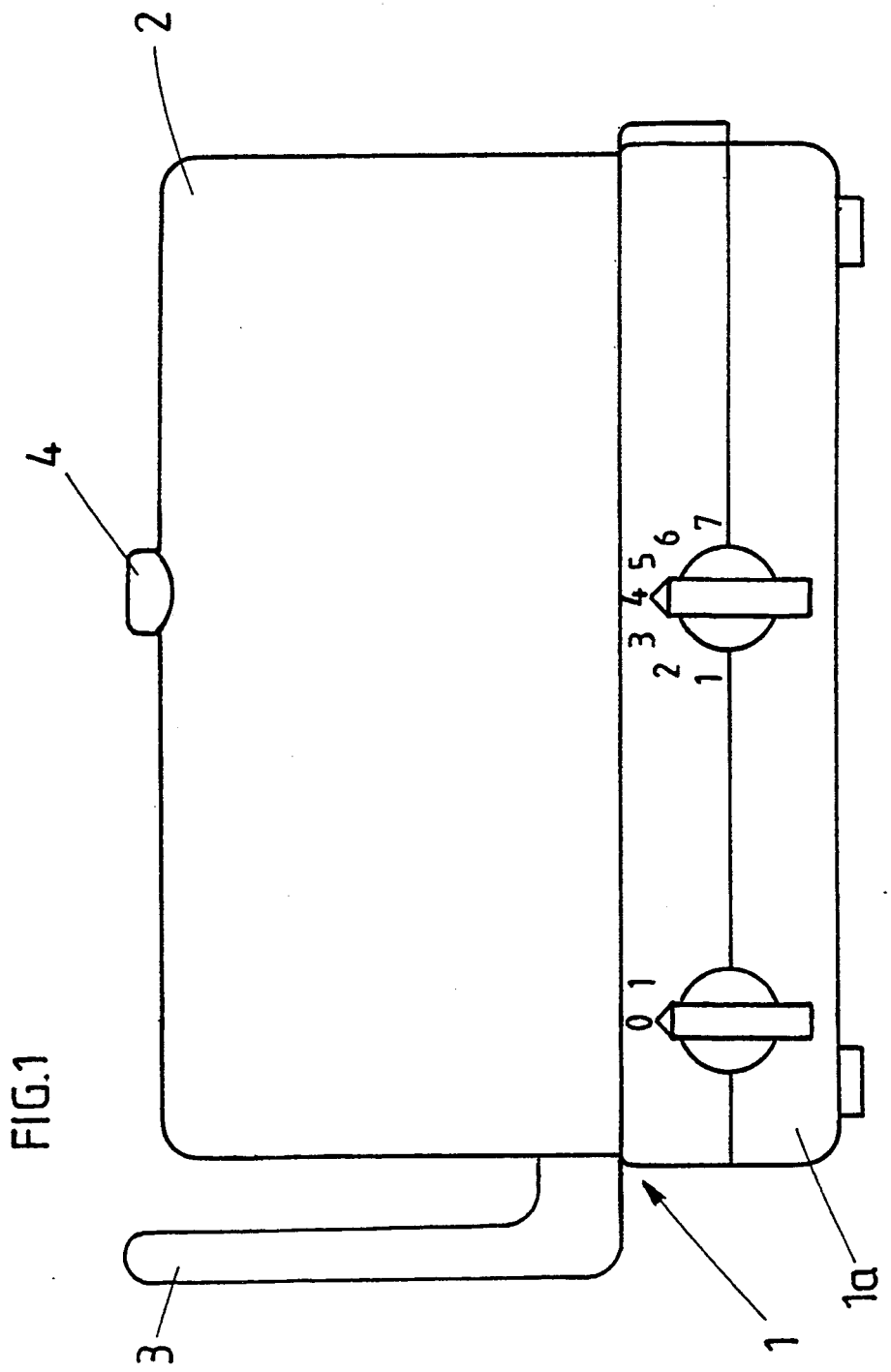
FIG. 1 represents a lateral view of the apparatus in its position of non-utilization, with the inverted reservoir covering the casing.

According to FIGS. 1 to 5, the apparatus comprises a casing 1 containing a hydraulic pump driven by an electric motor, a reservoir 2 of liquid with a handle 3 and a platform 12, on which a handpiece 17 in the form of a nozzle-holder and four spare nozzles 19 are placed. The electric motor can be connected by means of a cable (not shown) to an external mains socket. The handpiece 17 is connected by a flexible pipe 18 to the outlet orifice 10 of the casing 1 in communication with the outlet of the pump.

The casing 1 has a general stepped shape, the upper face of the top half serving as support face 5 for the reservoir 2 in operating position (FIG. 4), while the upper face of the bottom half serves as support face 8 for the platform 12. In the operating position of the reservoir 2, a valve 4 is in communication with the inlet orifice 6 of the casing, itself connected to the inlet of the pump. A positioning boss 7 formed on the casing 1 is provided to engage in a corresponding recess formed on the bottom of the reservoir 2 to ensure the correct operating position of said reservoir. In this operating position, illustrated in FIG. 4, the reservoir 2 covers the platform 12 and its stability is ensured by a small pillar 9 formed on support face 8. The arrangement is such that, in the position of non-utilization, the inverted reservoir serves as cover and covers the casing 1 and the platform 12 as well as the elements supported by the latter, with the exception of the lower part 1a of the casing, on the lateral side of which the control and adjustment buttons are situated (FIG. 1).

Figure 4:
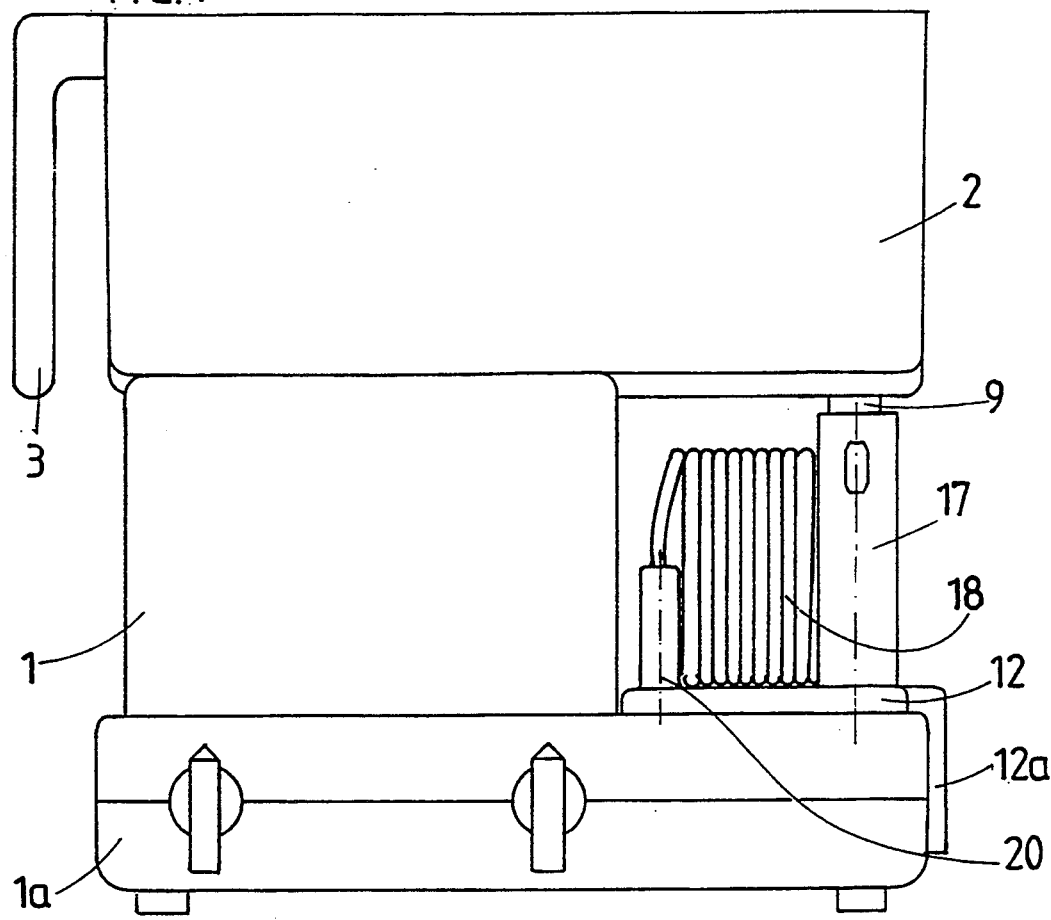
FIG. 4 is a lateral view of the apparatus, with the reservoir in operating position and the platform still in rest position, that is to say retracted below the reservoir.

Moreover, the height between the platform 12 and the bottom of the reservoir 2 in its operating position is slightly greater than the length of the handpiece 17 and of the nozzles 19 so that the latter can be placed in this space (FIG. 4).

Figure 11:
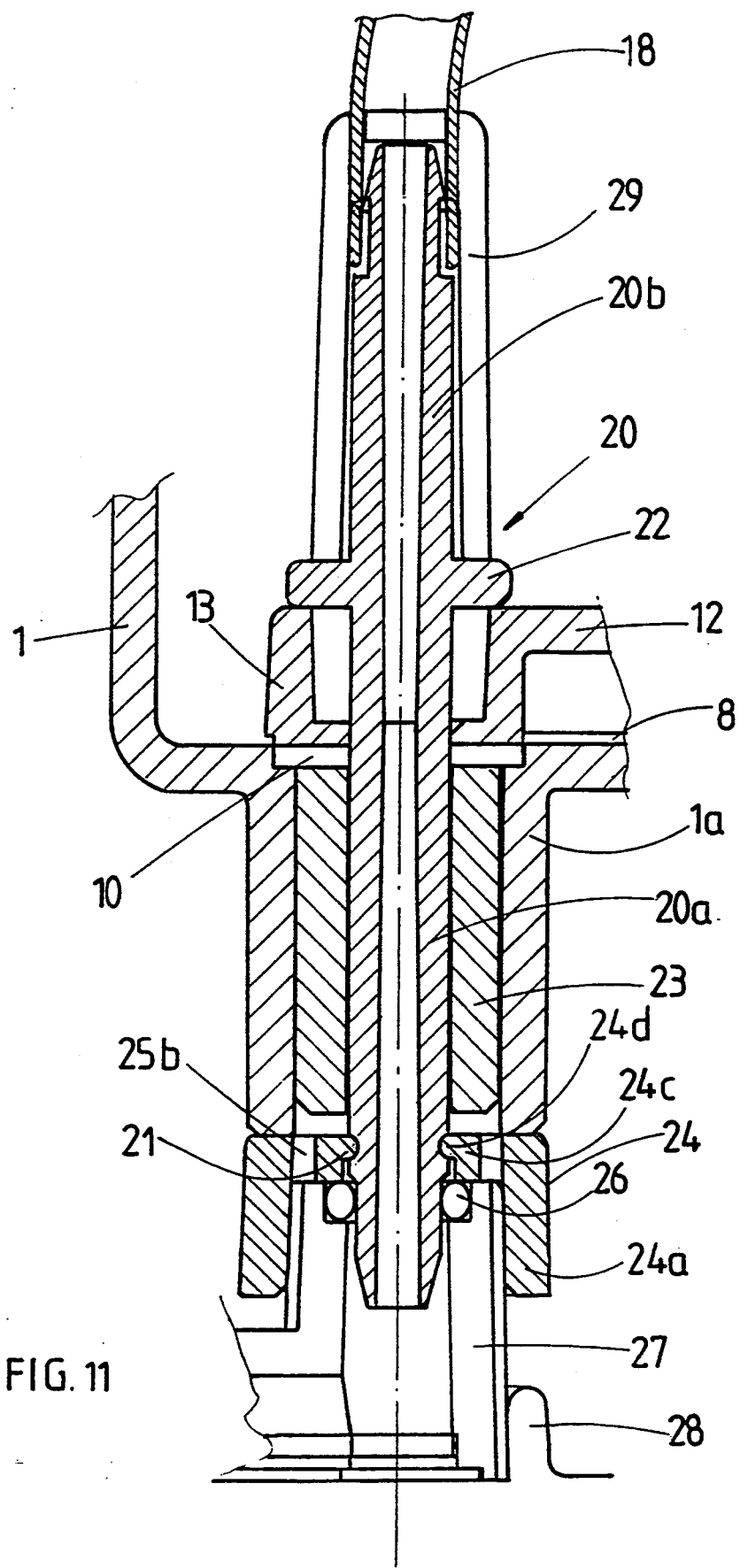
FIG. 11 is an enlarged view in cross-section of the arrangement of the turning adapter.

The platform is mounted so as to turn about the axis of the outlet orifice 10 of the casing, by means of a turning adapter 20 formed by a tubular connector (FIG. 11). The end of the pipe 18 connected to the outlet orifice 10 is also mounted rotationally movably about the axis of the pipe, therefore about the axis of the outlet orifice 10, by the same tubular connector 20. Therefore, the pipe 18 can turn in relation to the casing 1 and in relation to the platform 12 which can turn independently in relation to the casing 1. For this purpose, the platform 12 is formed by a piece with a sleeve 13 which is accommodated in a turning manner on the tubular connector 20 (FIG. 11).

Figure 5:
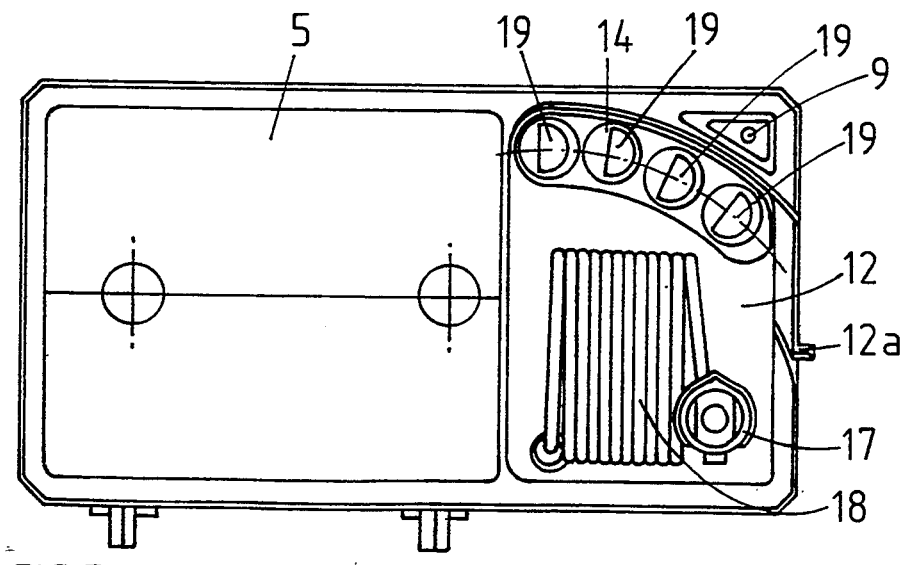
FIG. 5 is a view from above of the apparatus according to FIG. 4, with the reservoir removed.

As shown in FIGS. 3 and 3a, the platform 12 comprises a curved sector 14 with an excess thickness directed downwards, on which sector four openings 15 are provided, which are intended to receive four nozzles 19 (FIG. 5). The support face 8 of the casing 1 is equipped with a corresponding curved groove 11, in which the curved sector 14 of the platform 12 engages and can slide. The bottom of this groove 11 is equipped with an orifice 11a (FIG. 2) allowing flowing out of the water. The platform 12 is equipped on its lateral edge with a projection 12a which serves as a handle making it possible to operate it more easily and, in its corner directed towards the front of the apparatus, with a receiving opening 16 for the handpiece 17 (FIG. 3).

To use the apparatus, after having inverted the reservoir 2 and having placed it on the support face 5 in operating position, the platform 12 is pivoted partially into a position of preparation (FIGS. 6 and 7). In this intermediate position, the handpiece 17 is released from the reservoir 2, which makes it possible to fix on it a nozzle 19'. Then, the reservoir 2 can be filled with water and replaced on the casing without the risk of a flowing out of water through the handpiece taking place, as would be the case according to the principle of communicating vessels if the nozzle was not fixed.

In order that all the nozzles 19 supported by the platform 12 as well as this platform itself are freely accessible, the platform 12 is made to pivot completely as far as its most removed extreme position (FIGS. 8 and 9).

A catch can be provided to keep the platform in the intermediate position (FIGS. 6 and 7) or in the extreme position (FIGS. 8 and 9), as well as in the retracted position.

After having moved away from the casing 1 the handpiece 17, on which a nozzle 19' has been fixed, and before starting the treatment, the platform 12 is folded back into its retracted position so that it does not hamper the operation of said handpiece. This utilization position is illustrated in FIG. 10. Of course, in this utilization position, the fixed end of the pipe 18 is turned by means of the tubular connector 20 about its axis so that the pipe 18 can easily be moved away from the casing 1 in any direction so as to avoid contact with the casing in the course of utilization of the nozzle, as mentioned in the introduction.

Figure 12:
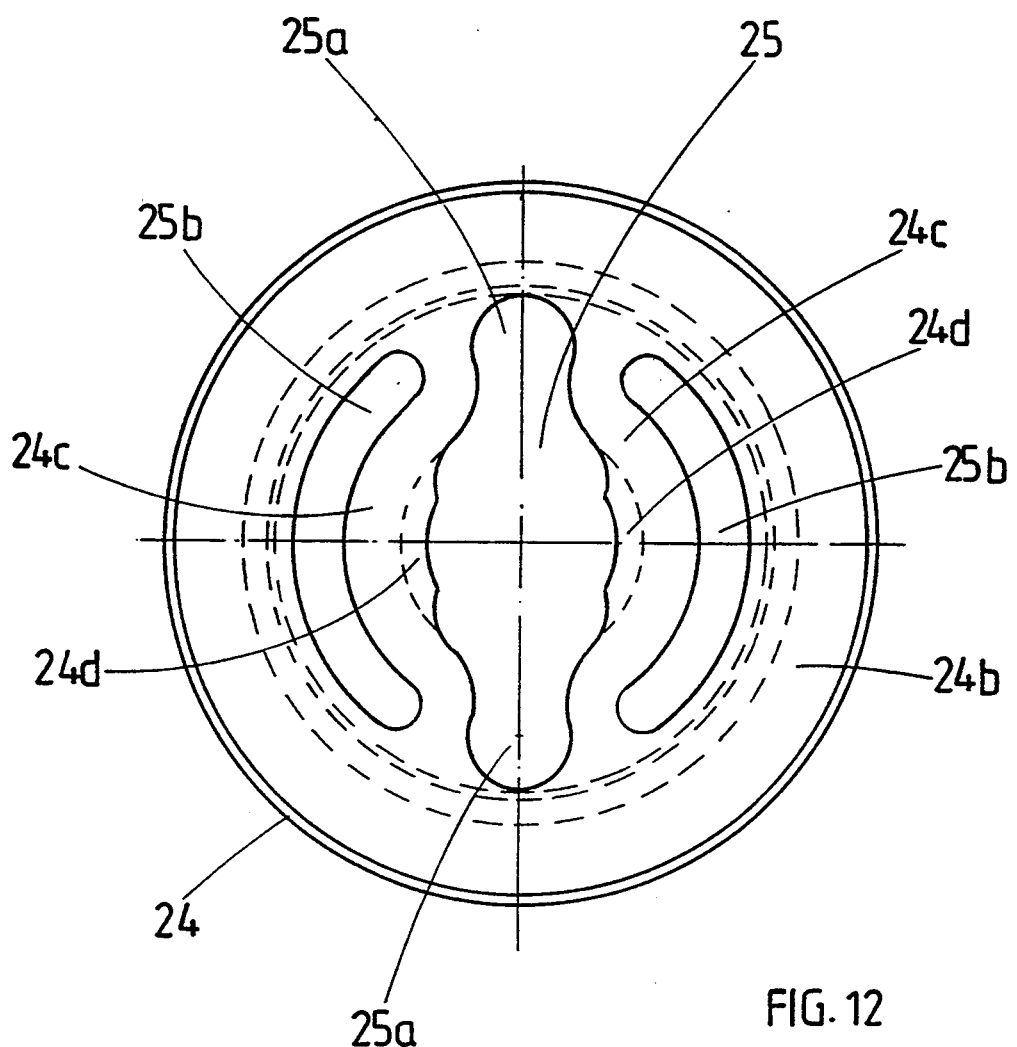
FIG. 12 is a view from below of the retention socket of the turning adapter.

FIG. 11 shows in a more detailed manner the arrangement of the turning adapter. The tubular connector 20 is inserted, via its relatively long internal part 20a, into the outlet orifice 10 of the lower part 1a of the casing 1 by means of a guide socket 23. The lower end of the tubular connector 20 penetrates into an opening of an internal part 27 of the casing which is fixed to the bottom 28 of said casing 1. To render the adapter impermeable, the internal end of the tubular connector is surrounded by an 0-ring joint 26 inserted into an annular groove of the part 27. Moreover, a retention socket 24 is provided, which is made of elastically deformable material and in the form of a hood, the peripheral wall 24a of which is clamped on the part 27. The radial wall 24b of the socket 24 has a central opening 25 (FIG. 12)

passed through by the tubular connector 20. This central opening 25 is extended by two diametrically opposite cutouts 25a which give it a generally elongate shape and, on either side of it, there are provided two other curved cutouts 25b which delimit two tongues 24c. The edge of these tongues 24c directed towards the center of the opening is equipped with diametrically opposite projections 24d which are provided to engage in an annular groove 21 formed on the periphery of the tubular connector 20 (FIG. 11). In this manner, the tubular connector 20 is held removably by a sort of catching of the projections 24d in the groove 21 and, if the tubular connector 20 is pulled towards the top, said projections 24d can move away towards the outside by virtue of the cutouts 25b which give a certain elasticity to the tongues 24c.

On the external part 20b of the tubular connector 20, the sleeve 13 of the platform 12 is placed, held in position by a collar 22 formed on the tubular connector, and, at the external end of the tubular connector 20, the pipe 18 is fixed clamped by a hoop 29. It can be seen that the tubular connector 20, with the pipe 18, can turn in the outlet orifice 10 while the platform 12 can itself turn independently about this tubular connector 20. If the tubular connector 20 is removed, the platform 12 can easily be demounted, the sleeve 13 thus being freed.

The invention is not limited to the embodiment which has just been described and modifications could be made without thus leaving the scope of the invention. In particular, as emerges from the description and from the utilization position illustrated in FIG. 10, the principal aim of the invention, namely the easy moving away of the pipe from the casing in the course of utilization, is achieved by virtue of the possibility of rotation of the end of the pipe in the outlet opening and therefore, in principle, it is not absolutely necessary that the platform can turn also.

It is also possible that the turning adapter be formed by the end itself of the pipe. If the platform is also pivotable, it is mounted rotatably about the pipe.

I claim:

1. An apparatus for dental hygiene including:
   a nozzle means;
   a liquid driving means within a housing, said liquid driving means providing liquid to said nozzle means;
   a liquid reservoir for providing liquid to said liquid driving means when said liquid reservoir is in an upright position, said liquid reservoir comprising a bottom surface and upwardly extending sidewalls;
   a lid for said reservoir wherein when said lid engages said reservoir, a portion of said lid extending from said sidewall thereby providing a gripping surface;
   a pedestal upon which said liquid driving means is attached, said pedestal including a post through which fluid communication between said liquid driving means and said nozzle means coaxially extends, said post providing a pivot for a platform, said platform including aperture means for engaging said nozzle means;
   whereby when said liquid reservoir is emptied and turned upside down, said liquid reservoir encases said liquid driving means and said nozzle means.

2. The apparatus of claim 1 wherein said liquid reservoir means further includes a handle.

3. The apparatus of claim 2 including hinge means for attaching said lid to said sidewalls.

* * * * *